(12) United States Patent
Carlsen et al.

(10) Patent No.: US 8,108,024 B2
(45) Date of Patent: Jan. 31, 2012

(54) REGISTRATION OF MULTI-MODALITY IMAGES

(75) Inventors: Ingwer C. Carlsen, Hamburg (DE);
Lingxiong Shao, Saratoga, CA (US);
Angela J. DaSilva, Danville, CA (US);
Steffen Weiss, Hamburg (DE); Micheal J. Petrillo, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1195 days.

(21) Appl. No.: 11/721,714

(22) PCT Filed: Dec. 5, 2005

(86) PCT No.: PCT/IB2005/054066
§ 371 (c)(1),
(2), (4) Date: Jun. 14, 2007

(87) PCT Pub. No.: WO2006/064400
PCT Pub. Date: Jun. 22, 2006

(65) Prior Publication Data
US 2009/0326362 A1 Dec. 31, 2009

Related U.S. Application Data

(60) Provisional application No. 60/636,281, filed on Dec. 15, 2004.

(51) Int. Cl.
*A61B 5/05* (2006.01)
(52) U.S. Cl. ........ 600/407; 600/425; 600/427; 382/128; 382/173; 382/294
(58) Field of Classification Search .................. 600/407, 600/425, 427; 382/294, 128, 173
See application file for complete search history.

(56) References Cited

U.S. PATENT DOCUMENTS

| 5,391,877 | A | | 2/1995 | Marks |
| 5,672,877 | A | * | 9/1997 | Liebig et al. ............. 250/363.04 |
| 5,871,013 | A | | 2/1999 | Wainer et al. |
| 6,333,971 | B2 | * | 12/2001 | McCrory et al. ............... 378/162 |
| 6,650,925 | B2 | * | 11/2003 | Wang ............................ 600/410 |
| 7,002,345 | B2 | * | 2/2006 | Jara ................................ 324/310 |
| 7,158,692 | B2 | * | 1/2007 | Chalana et al. ............... 382/294 |
| 7,197,171 | B2 | * | 3/2007 | Yuzefovich et al. .......... 382/131 |

(Continued)

OTHER PUBLICATIONS

Andersson, J. L. R., et al.; A Method for Coregistration of PET and MR Brain Images; 1995; Journal of Nuclear Medicine; 36(7)1307-1315.

(Continued)

*Primary Examiner* — Tse Chen
*Assistant Examiner* — Baisakhi Roy

(57) ABSTRACT

A system for generating registered diagnostic images (58, 62), such as nuclear and magnetic resonance (MR) images, of a subject includes a nuclear imaging device (10) for generating emission diagnostic images (58) and optionally also intermediate transmission or emission images (56). A second imaging device (12), such as an MR imaging device generates magnetic resonance diagnostic images (62) and optionally also intermediate images which are more readily registered with images from the nuclear imaging device than the diagnostic MR images. Processing for the images includes a preprocessing portion (64) for generating a transform for aligning common anatomical structures in images (56, 58, 60, 62) generated by the nuclear imaging device and the MR imaging device and a diagnostic image registration portion for applying the transform to bring the emission and magnetic resonance diagnostic images into registration (58, 62).

22 Claims, 1 Drawing Sheet

U.S. PATENT DOCUMENTS

| | | | |
|---|---|---|---|
| 7,558,439 B2 * | 7/2009 | Weese et al. | 382/294 |
| 2004/0054278 A1 * | 3/2004 | Kimchy et al. | 600/407 |
| 2006/0004274 A1 * | 1/2006 | Hawman | 600/407 |
| 2006/0099148 A1 * | 5/2006 | Fisher et al. | 424/9.34 |
| 2007/0243136 A1 * | 10/2007 | Fisher et al. | 424/9.32 |

OTHER PUBLICATIONS

Carrington, C.; Innovative Agents Boost Molecular MR's Sensitivity-Nanoparticles Open Doors to Earlier Cancer Detection; 2003; Molecular Imaging Outlook (Online); http://www.diagnosticimaging.com/molecularimagingoutlook/2003jun.

Fei, B., et al.; Registration and Fusion of SPECT, High-Resolution MRI, and Interventional MRI for Thermal Ablation of Prostate Cancer; 2004; IEEE Trans. on Nuclear Medicine; 51(1)177-183.

Kneoaurek, K., et al.; Medical Image Registration; 2000; Europhysics News; 31(4)1-8.

Lanza, G., et al.; Molecular Imaging and Therapy of Solid Tumors with a Novel-Spacific Nanoparticle Targeted to the Neovasculature; 2004; UIP Investigators Meeting Online; http://www.otir.cancer.gov/meetings/abstracts/lanza04.html.

* cited by examiner

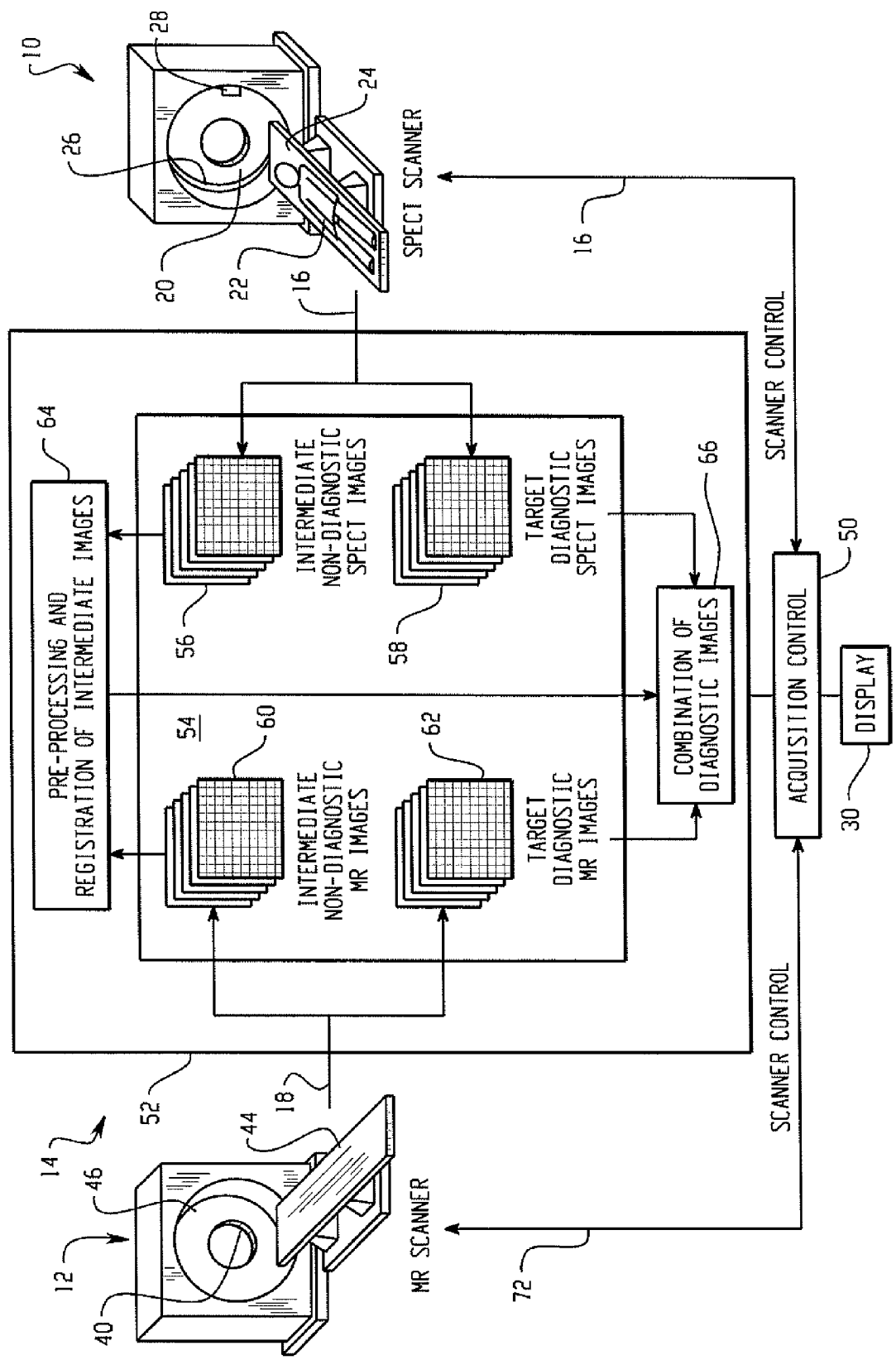

REGISTRATION OF MULTI-MODALITY IMAGES

CROSS REFERENCE TO RELATED APPLICATIONS

This application claims the benefit of U.S. provisional application Ser. No. 60/636,281 filed Dec. 15, 2004, which is incorporated herein by reference.

The present invention relates to the registration of images from different imaging modalities so that such images may be displayed together, superposed upon one another. It finds particular application in conjunction with the registration of single photon emission computerized tomography (SPECT) images with images generated by magnetic resonance (MR) imaging, and will be described with particular reference thereto. However, it is to be appreciated that the present exemplary embodiment is also amenable to the registration of images from other modalities.

There are many fields in which it is useful to image a subject using different imaging modalities. Some modalities, such as MR and X-ray computed tomography (CT), provide detailed anatomical information about the subject in the form of an X-ray image or a magnetic resonance image. Other modalities, including nuclear imaging techniques such as SPECT and positron emission tomography (PET), provide information about different structures not visible in another modality, or functional information about metabolic or physiological phenomena occurring within the subject, such as by the introduction into the subject of a radioactive marker attached to a physiological tracer.

While images from different modalities can be examined side by side, information about the spatial relationship between the structures shown in one image with those of the other are often useful, for example, the position of a tumor in relation to adjacent tissue or bone structures. There is a rapidly growing demand, particularly in the medical community, to combine functional information provided by SPECT or PET with anatomical information provided by MR to relate physiological/metabolic phenomena with the underlying anatomy. It is often useful to display the images in superposition one upon the other. For the superposition to be accurate, areas representing a particular position in the subject in one image should be accurately positioned in relation to corresponding areas in the other image. The process of achieving this alignment is known as "registration." For accurate registration, it is desirable for each point in one image to be mapped to the corresponding point on the second image.

A variety of techniques for registration of images of different modalities, particularly in the medical imaging field, have been proposed. In one method, images in two modalities are obtained contemporaneously or substantially contemporaneously, without moving the subject or by shifting the subject a precisely known distance between scanners. Dedicated scanners have been developed for PET/CT and SPECT/CT imaging which alleviate registration problems to a degree. However, some imaging devices are not suited to use in close proximity. For example, the magnetic fields generated in an MRI device can affect the acquisition of SPECT data. Additionally, providing two modalities in a single imaging device adds to the complexity and cost of the device. Accordingly, it is desirable to register images which have been generated independently, i.e., spaced in time and/or location.

The registration of images from different modalities includes deriving a mathematical relationship for mapping the images to be registered. The software which performs the mapping includes methods for identifying common features, for example, based on detection and comparison of intensities or intensity distributions, or detection and comparison of edges or of geometric structures. For example, methods based on matching intensities of images to be registered include changing transformation parameters to minimize variations.

One difficulty in registering independently acquired images from SPECT and MR is that the physical principles underlying the image generation process are very different and unrelated, thus there are few, if any, accurately identifiable common features in the images from these two modalities. The more specific a SPECT tracer, the less general anatomical contrast it will produce that will also appear in the related MR image. In the extreme case, the SPECT image shows only a few, highly specific hot spots without any visible relation to the surrounding anatomy. The lack of common information, i.e., nuclear medicine images do not include detailed bone or organ structure, while MR images do not include functional information, means that the two images lack the information for matching them accurately.

Fiducial markers which show in the images of both modalities have been developed to assist in registering images from different modalities. However, fiducial markers are not particularly effective in tissue remote from bone structures as the tissues tend to move.

Software packages have been developed for registration of independently acquired images from PET and CT. The technique makes use of isotope radiation transmission images which are acquired together with diagnostic data by the PET system at different energies for the purpose of subsequent attenuation correction of the reconstructed images generated from the diagnostic data. The transmission scans are based on the same physical principles as CT and can be compared with those from the CT device. The success of PET and CT registration has stimulated a demand for combination of SPECT and MR data.

U.S. Pat. Nos. 5,871,013 to Wainer, et al. and 5,672,877 to Liebig, et al., for example, disclose methods of registering functional nuclear medicine emission images with other modality images, such as x-ray images, by using the transmission image in the registration process. Since the transmission image is customarily obtained on the same imaging equipment as the functional emission image, it can be assumed to be co-registered with the emission image (i.e. the same pixel address in the image frame corresponds to the same position in the subject).

In some cases, a SPECT emission image is acquired simultaneously with a transmission image (sometimes referred to as a SPTCT image), which is obtained by placing a source of radiation on the opposite side of the subject from a detector so that the radiation enters the subject and some passes through to reach the detector. This provides an image which provides information regarding the attenuation and scattering characteristics of the subject. The transmission image is used to correct the emission image for the different attenuation and scattering occurring in different areas of the subject. In an emission image, photons emitted from different depths or from different structures of the subject undergo different attenuation and scattering, leading to varying intensities in the image which are not related to the metabolic function in the body. The transmission image effectively provides information about the differing attenuation and scattering and allows correction of the emission image.

However, the SPECT emission images include information about function but do not provide significant information about the structure of the subject. Thus, they do not relate directly to the anatomical MR images.

In accordance with one aspect of the present exemplary embodiment, a system for generating registered nuclear and MR diagnostic images of a subject is provided. The system includes a nuclear imaging device for generating at least emission diagnostic images and an MR imaging device for generating at least magnetic resonance diagnostic images. Means are provided for generating a transform for aligning common anatomical structures in images generated by the nuclear imaging device and the MR imaging device and for applying the transform to bring the emission and magnetic resonance diagnostic images into registration.

In accordance with another aspect of the present exemplary embodiment, a method for generating registered nuclear and MR diagnostic images of a subject is provided. The method includes generating at least an emission diagnostic image of the subject with a nuclear imaging device and generating at least a magnetic resonance diagnostic image with an MR imaging device. A transform is generated for aligning common anatomical structures in images generated by the nuclear imaging device and the MR imaging device. The transform is applied to bring the emission and magnetic resonance diagnostic images into registration.

In accordance with another aspect of the present exemplary embodiment, a method for registration of images of different modalities is provided. The method includes generating a first diagnostic image of a subject with a nuclear imaging process of a first modality, generating a first intermediate image of the subject which is co-registered with the first diagnostic image, generating a second diagnostic image of a subject with an imaging process of a second modality, and generating a second intermediate image of the subject which is co-registered with the second diagnostic image. A transformation is derived which registers the first and second intermediate images and applied to register the first and second diagnostic images.

In accordance with another aspect of the present exemplary embodiment, a system for registration of images of different modalities is provided. The system includes a first imaging device for generating a first diagnostic image of a subject with an imaging process of a first modality, the first imaging device being configured for generating a first intermediate image of the subject which is co-registered with the first diagnostic image, and a second imaging device for generating a second diagnostic image of a subject with an imaging process of a second modality, the second imaging device being configured for generating a second intermediate image of the subject which is co-registered with the second diagnostic image. A control and processing system instructs the first and second imaging devices to acquire the first and second diagnostic images and first and second intermediate images, the control and processing system deriving a transformation which registers the first and second intermediate images and applies the transformation to register the first and second diagnostic images.

An advantage of at least one embodiment of the present invention is that it enables the fusion of SPECT and MR images.

Another advantage of at least one embodiment of the present invention resides in increased accuracy of registration of images from different modalities.

Another advantage of at least one embodiment of the present invention resides in the registration of independently acquired images.

Still further advantages and benefits of the present invention will become apparent to those of ordinary skill in the art upon reading and understanding the following detailed description of the preferred embodiments The invention may take form in various components and arrangements of components, and in various steps and arrangements of steps. The drawing is only for purposes of illustrating the preferred embodiments and is not to be construed as limiting the invention.

FIG. 1 is a schematic drawing of a system for the acquisition and use of intermediate SPECT and MR images for the registration/fusion of diagnostic SPECT and MR images.

A method for registration of images from more than one imaging modality includes generating an image in one or both modalities which possesses registrable features. In one embodiment, the image (or images) having registrable features is an intermediate image, which need not be of diagnostic quality and which can be assumed to be co-registered with an image to be used for diagnostic purposes (a "diagnostic image"). Suitable software transformations are generated which register the intermediate image from one modality with the intermediate image or diagnostic image from the other modality. The generated transformations are then applied to register diagnostic images from the two modalities. In one embodiment, intermediate images from one or both modalities are generated by protocols which differ from the standard data acquisition protocols which are used for generating diagnostic images. In another embodiment, a tracer which is visible in both modalities allows registration of diagnostic images.

In the case of SPECT, the intermediate image may be a transmission image or the intermediate image may be an emission image formed with a tracer which is visible in the other imaging modality with which it is to be registered. In the case of MR/SPECT registration, the intermediate MR image may be an image of lower resolution than the diagnostic image or generated with a different pulse sequence from that used for the diagnostic image, which different pulse sequence is selected to highlight features visible on the SPECT image with which it is to be registered. While particular reference is made to the registration of images from a nuclear imaging process such as SPECT, with those from a non-nuclear imaging process, such as MR, it will be appreciated that the methods described may be applied to the registration of images from other sources, such as combinations of two or more selected from SPECT, PET, MR, and CT.

Particular reference is made herein to the registration of independently acquired images i.e., those which are generated at spaced locations and/or are spaced in time, such that the subject, e.g., a patient's body or a portion thereof, cannot be assured to be in the same orientation with respect to the detector(s) of the second imaging device as the orientation to the first. However, the method also finds application in the registration of images which are acquired substantially contemporaneously by imaging devices of different modalities located in the same physical structure, such that they can be operated without moving the patient from one device to another or at least without the patient leaving the patient support pallet.

In one embodiment, one or both the SPECT and the MR imaging devices is flexible enough to acquire additional data supporting the registration task. The additional data for the intermediate images do not necessarily have to be of diagnostic quality as they can be used primarily for registration purposes (and optionally also for attenuation correction) and thus are not intended to be viewed by the physician. Acquisition of the data for registration (i.e., the intermediate image or images) may entail modifications to the standard protocols typically used for the conventional, i.e. independent, acquisition of SPECT and MR data. While this may entail extended acquisition protocols for one or both modalities, the use of less than diagnostic quality intermediate images results in a minimal extension of time to the overall imaging procedure.

In specific embodiments, the method may employ dedicated acquisition protocols involving the acquisition of intermediate, non-diagnostic SPECT and/or MR images and their dedicated processing. One purpose of providing intermediate MR images is to provide contrast that can be directly related with the contrast in the intermediate SPECT images, facilitating their software-based registration. The intermediate MR images are acquired in such a way that they can be considered as co-registered with the diagnostic MR images. For example, the data for the intermediate and diagnostic MR images are acquired at closely spaced time intervals, preferably the data acquisitions for the images are interleaved. It can then be assumed there is no or appreciably no patient movement which would cause the images not to be inherently co-registered. Similarly, the intermediate SPECT images are acquired in such a way that they also can be considered as co-registered with the diagnostic SPECT images. On the basis of the software-based registration of the intermediate SPECT images with the intermediate MR images (or with respective diagnostic images where an intermediate image is not generated in one modality), the registration/fusion of the diagnostic MR images with the diagnostic SPECT images is more readily achieved than is generally possible on the basis of the diagnostic images alone. As the intermediate MR images do not have to be of diagnostic quality, they can be acquired extremely rapidly so that they will not significantly lengthen the standard acquisition protocols.

With reference to FIG. 1, a schematic illustration of a system for imaging in two (or more) modalities and image registration is shown. The system includes first and second imaging devices 10, 12. In the illustrated embodiment, the first device 10 is configured for SPECT imaging and the second device 12 is configured for MR imaging, although it is to be appreciated that the two devices 10, 12 may have additional imaging capabilities. Data for reconstructing images is supplied by the first and second imaging devices 10, 12 to a control and processing system 14 via wired or wireless links 16, 18. The control and processing system 14 may be embodied in a personal computer, computer network, or other suitable hardware/software.

The first device 10 includes an imaging region 20 in which a patient 22 lies or is transported therethrough on a moveable support 24. One or more radiation detectors 26 are positioned adjacent to the patient to monitor and record emitted radiation. The detector 26 is suitable for whichever imaging modality is chosen. In the case of SPECT imaging, gamma or scintillation detectors are optionally used. The scintillation detector includes a scintillator comprising a large scintillation crystal or matrix of smaller scintillation crystals. In either case, the scintillator is viewed by a matrix of sensors, such as photomultiplier tubes ("PMTs"). A collimator, which includes a grid- or honeycomb-like array of radiation absorbent material, is located between the scintillator and the subject being examined to limit the angle of acceptance of radiation which impinges on the scintillator. Each radiation event impinging on the scintillator generates a corresponding flash of light (scintillation) that is seen by the PMTs. Based on the outputs from the PMTs, radiation events are mapped, which include the energy and position of radiation rays impinging the scintillator. The image quality of the SPECT images is typically determined by a count sensitivity of the detector and the geometry of the collimator. Alternatively, a cadmium zinc telluride (CZT) based detector is used which detects photons directly without a scintillation detector.

Nuclear emission imaging, such as SPECT, employs a source of radioactivity which is introduced to the patient's body. In one embodiment, the source includes a radioactive marker which is attached to a physiological tracer. The radioactive marker for SPECT is generally a radioisotope that undergoes gamma-ray decay at a predictable rate and characteristic energy, which is monitored and recorded by the detector 26. The tracer is injected in the blood of the patient and fixes to specific cells in the patient having a particular metabolic activity. The tracer and associated radioactive marker thus tend to be concentrated according to physiological function. The detector 26 detects the radioactive marker and provides one or more corresponding images whose intensities correspond to the amount of radioactive marker in each region. The results of several scans may be combined together in a tomography process to provide three dimensional emission images.

SPECT imaging finds application in the study of the circulatory system and of selected organs or tissue. One particularly important application of these techniques is in the detection of tumors in the body. Such tumors are prominent in an emission images because of the high metabolic activity in and around the tumor.

For the production of a transmission image using the device 10, a radioactive source 28 is provided on an opposite side of the patient from the detector 26. The detector 26 and/or the source 28 may be rotated or indexed around the patient to monitor the emitted radiation from a plurality of directions.

The signals from the detector 26 are supplied to the imaging control and processing system 14 which produces image data for display on a display 30, such as a screen or paper printout. Based on information such as detected position and energy, the radiopharmaceutical distribution in the body is determined and an image of the distribution is reconstructed to study, for example, the circulatory system, radiopharmaceutical uptake in selected organs or tissue, or the like.

In a similar way, signals are generated by the second imaging device 12, which is of a different modality to the first imaging device 10. The second device 12 includes an imaging region 40 in which a patient lies on a moveable support 44. One or more radiation detectors 46 are positioned adjacent to the patient. For example, in an MR imaging device, a magnetic coil (not shown) around the imaging region 40 causes proton resonance within the patient which is detected by the detector 46. The signals from the detector 46 are supplied to the imaging control and processing system 14 which produces image data for display on the display 30.

It will be appreciated that the processing software for reconstructing the images from the first and second devices 10, 12 may be located in a single processing system 14, as shown, or may be distributed. In the illustrated embodiment, the control and processing system 14 includes an acquisition control portion 50 which directs the imaging devices 10, 12 to perform the appropriate steps for acquiring data for generating the intermediate and diagnostic images and a reconstruction and registration portion 52. The portion 52 includes an image reconstruction portion 54 for generating intermediate and diagnostic images 56, 58, 60, 62, a preprocessing portion 64 for registering intermediate images 56, 60 (or an intermediate image with a diagnostic image). More specifically, the preprocessing portion determines a linear or non-linear transform which brings the alignment images into registration. A diagnostic image registration portion 66 registers diagnostic images from the first and second devices 10, 12 using the transform determined in the registration of one or more intermediate images. For some applications, however, one or both of the diagnostic images can also function as the alignment image(s), as discussed below. The control and processing system instructs the devices 10, 12 to perform the scans and acquire intermediate images, where appropriate, for registration. Wired or wireless links 70, 72 connect the control and acquisition portion with the scanners 10, 12.

Various registration sequences are proposed, as follows:

In a first method (M1), intermediate alignment-only images 56, 60 and diagnostic images 58, 62 which are inherently co-registered are generated for both devices 10, 12. The registration process includes developing a mathematical transformation which maps the first and second intermediate images 56, 60 into registration and applying the same transformation (after proper rescaling to the resolution of the diagnostic images) to the diagnostic images 58, 62. The transformation is generated by the software in the reconstruction and registration portion 52 and includes the mathematical manipulations of the data whereby a number of points in the two intermediate images 56, 60 are registered.

A fused image, in which the two registered diagnostic images are superimposed, added, or otherwise combined, can thus be generated by the diagnostic image registration portion 66 and shown on the screen 30.

In a second method (M2) diagnostic images 58, 62 are generated for both devices 10, 12 and an intermediate image 56 is generated for the first device 10. The intermediate image 56 from the first device has sufficient common structure with the second diagnostic image that the two are registrable without the need for generating an intermediate image with the second device. (In this embodiment, the preprocessing portion 64 registers the intermediate image 56 with the second diagnostic image 62.) Thus, the method includes developing a mathematical transformation which maps the intermediate image 56 from the first device with the diagnostic image 62 from the second device and applying the same transformation to map the two diagnostic images 58, 62 to create a fused image.

In a third method (M3) diagnostic images 58, 62 are generated for both devices 10, 12 and an intermediate image 60 is generated for the second device 12. The intermediate image 60 from the second device is registrable with the diagnostic image 58 from the first device, without the need for generating an intermediate image with the first device. (In this embodiment, the preprocessing portion 64 registers image 60 with image 58.) Thus, the method includes developing a mathematical transformation which maps the intermediate image 60 from the second device with the diagnostic image 58 from the first device and applying the same transformation to map the two diagnostic images 58, 62 to create a fused image.

In a fourth method (M4) diagnostic images 58, 62 are generated for both devices 10, 12. Use of appropriate pharmaceutical agents allows the diagnostic images to be directly registrable, without the need for intermediate images of either modality. In this embodiment, the preprocessing portion 64 generates the transform from the diagnostic images.

The MR and SPECT image data for any of the above methods are acquired independently from each other on different scanners 10, 12. The intermediate and diagnostic SPECT data (where both are used) are acquired in direct succession, superimposed, or interleaved to minimize patient/organ motion between the acquisitions. Similarly, the intermediate and diagnostic MR data (where both are used) are acquired in direct succession or interleaved to minimize patient/organ motion between the acquisitions. The acquisition control 50 of the control and processing system 14 is supplied with information which enables it to plan the MR and SPECT acquisitions. Included in this information may be information as to whether a transmission scan will be available, which radiopharmaceutical or other tracers will be used on the SPECT side, and which field-of-view will be covered by the SPECT scans. This information is then used to determine an appropriate pulse sequence to be used for the acquisition of intermediate MR images (where used).

The intermediate and diagnostic SPECT (or PET) and MR images may be generated in various ways. Four methods are provided by way of example, although it will be appreciated that these methods may be combined or other methods employed.

1) Combination of Low-Resolution Proton Density MR Scans with SPECT Attenuation Maps This method includes the generation of four images, as described in method M1 above. A SPECT emission image is generated with device 10 using standard acquisition processes. A transmission map is generated concurrently or in close temporal proximity with the SPECT device 10 which serves as an intermediate alignment image for the SPECT emission diagnostic image. The transmission map is inherently co-registered with the emission image (for example, by being generated by the same device 10 either closely in time or overlapping in time). The SPECT emission image is a diagnostic image, i.e., one which has sufficient resolution to be suitable for diagnostic purposes and may show few, if any, registrable features which could serve to register the image with an MR image. The transmission map, however, has many of the characteristics of a low-quality CT scan. Depending on scan time selected and the energy of the external radiation source 28, a registrable feature or features, such as the body contours and/or outlines of bones and some major organs shows on the intermediate transmission image. The transmission map is selected to have a greater extent of registrable anatomical features than the diagnostic image.

At some time which may be before or after the SPECT images are generated, the MR intermediate and diagnostic images are generated by interleaving proton density sequence segments into a selected diagnostic plan sequence. The MR intermediate image is inherently co-registered with the MR diagnostic image (in this case, by being generated by the same device 12, either closely in time or overlapping in time). The intermediate MR proton density image includes registrable features, such as major organs, bone, body contours, and the like, which can be registered with the corresponding registrable features of the transmission image from the SPECT device 10.

In a preferred embodiment, the MR intermediate image is generated at a lower resolution than the MR diagnostic image to match the resolution of the intermediate transmission image. The MR intermediate and diagnostic images may thus use different pulse sequences which differ in length. Typically, lower resolution images use shorter sequences. The MR intermediate image may thus have a resolution which is closer, than that of the MR diagnostic image, to the resolution of the intermediate, transmission image from the device 10. In one embodiment, the MR intermediate image has a resolution which closely matches the resolution of the SPECT transmission image. Accordingly, the time taken for the low resolution proton density scans for forming the intermediate MR image is negligible compared to the time taken diagnostic MR scans and will hardly extend the standard MR acquisition protocols, while being patient safe.

The intermediate image from the first device 10 is registered with the intermediate image from the second device 12. The registration process includes the use of software which determines the closest fit between the images, typically by focusing on the registrable features which appear in both images.

2) Combination of MR Scans with Dual Tracer SPECT Studies

In this method, an intermediate image and corresponding diagnostic image from the first device 10, and a diagnostic image and optionally also an intermediate image from the second device 12 are generated and the method M1 or M2, described above, is used in the registration process.

The diagnostic SPECT image is generated using a primary tracer and the intermediate SPECT image is generated using a secondary tracer different from the primary tracer. The tracers both have a radionuclide which shows up in the respective SPECT emission scan, the two radionuclides being of different energies which the SPECT device can distinguish. The primary SPECT tracer may be highly specific to a particular organ or other location under investigation. The secondary tracer concentrates on bones, specific organs, blood, or other tissue types that are also visible in either the diagnostic MR scan or in a separate, low-resolution MR alignment scan.

For example, the secondary tracer can highlight the circulatory system and the MR alignment image can be a black blood angiographic image. A suitable primary tracer is In111-labeled capromab pendetide (ProstaScint™) for detecting and localizing primary and metastatic prostate cancer. A suitable secondary tracer is Tc-99m-labeled Red Blood Cells (RBC) to image the vasculature.

In one embodiment, the secondary SPECT tracer is primarily used to produce SPECT contrast that directly relates to MR contrast and can be registered with an MR scan. As with the embodiment (1) discussed above, due to the truly or at least nearly simultaneous acquisition of the two SPECT images, the primary SPECT image is co-registered to the secondary SPECT image. Where an intermediate MR image is generated, this is co-registered with the diagnostic MR image. The SPECT diagnostic image can thus be automatically aligned with the MR diagnostic image by applying the same transform as developed for the registration of the intermediate SPECT image with the MR image (diagnostic or intermediate) as discussed above.

The primary tracer may include a gallium or indium isotope as radionuclides and the secondary tracer may include technetium, which has a different energy associated with the photons generated when the element decays. The radionuclide marker is attached to a physiological tracer. The physiological tracer for the primary tracer is different from that of the secondary tracer. For example, the physiological tracer for the secondary tracer is selected to bind to organs and/or other body parts which show up in the MR image while the physiological tracer in the primary tracer is selected to bind specifically, or more specifically, to the target organ or region under investigation. In one embodiment, the primary tracer is In-111 labeled Pentetreotide (OctreoScan™) for detecting and localizing primary and metastatic neuroendocrine tumors bearing somatostatin receptors. The secondary tracers can be Tc-99m-labeled methylene diphosphonate (MDP) for bone SPECT. The secondary MR scan is a proton density or other scan which emphasizes bone. Alternatively, the bone structure can be generated from the diagnostic MR scan in a post-processing operation.

When the secondary tracer uses a bone agent, the tracer highlights bone on the intermediate SPECT image. The intermediate SPECT image can be registered directly on an MR diagnostic image performed with a pulse sequence which highlights bone. Thus, method M2 can be used. In some cases, it may still be advantageous to form a low resolution MR scan for easier mapping with the intermediate SPECT image, using method M1.

The primary SPECT tracer can be combined with the secondary SPECT tracer and injected into the subject.

3) Use of Combined SPECT-MR Tracers

In this embodiment, a tracer which provides contrast in both SPECT and MR is introduced to the subject. The tracer generates the related image structures which can be used for the unambiguous registration/fusion of SPECT with MR data. This method may follow the procedure for method M4 or M3, although it may use other methods, such as M1 or M2.

In one embodiment, a diagnostic image is generated using the first device 10 and a diagnostic and an intermediate image are generated with the second device 12 (M3). The intermediate image is generated with a pulse sequence which is specific to the tracer. In another embodiment, the tracer is visible using the same pulse sequence as the MR diagnostic image and the intermediate image need not be performed (method M4).

In one embodiment, a dual modality SPECT-MR tracer is formed by attaching SPECT-visible radioactive nuclei and nanoparticles formed of an MR contrast altering magnetic material to each other or to a common carrier. Other MR contrast agents, such as radionuclides which show up in MR imaging, are also contemplated. Due to the much higher sensitivity of SPECT compared to MR (nano-mols of radionuclide correspond in detection levels to milli-mols of nanoparticles), only small amounts of radioactive additives are sufficient for producing useful dual-modality image contrast.

The dual modality tracer is tailored to accumulate in a particular area of the body of interest, for example, the specific structure which is the subject of the SPECT diagnostic imaging or a surrounding or closely positioned region. This region shows up as contrast in both imaging modalities, thereby allowing accurate registration. Typical coatings include lipids.

The nanoparticles may be up to about 1000 nanometers in length, typically less than 500 nanometers, and in one embodiment, about 200-250 nanometers in length. In one embodiment, a cluster of nanoparticles is loaded with a radionuclide, such as technetium 99 or indium 111 which shows up in SPECT as well as a magnetic material or a radionuclide such as gadolinium or gallium 67, which show up as a bright spot on an MRI. For example, the nanoparticles may comprise lipid-encapsulated liquid perfluorocarbon nanoparticles, about 200-250 nanometers in length, each nanoparticle carrying about 10 to about 500 indium atoms per nanoparticle and optionally from about 1000-50,000 MR-enhancing atoms, such as gadolinium atoms, per particle.

While both MR and SPECT visible tracers may be provided on the same nanoparticles, it is also contemplated that the MR and SPECT tracers be attached to separate nanoparticles and a combination of the two types of nanoparticles injected into the subject. In this latter embodiment, the coating of the nanoparticles is the same in terms of the tendency to accumulate in a particular organ or other location, such that both types of nanoparticle tend to accumulate preferentially in the same location.

4) Combination of MR Scans with Dual Tracer SPECT Studies Using Combined SPECT-MR Tracers This embodiment combines features of dual tracer studies and combined SPECT-MR tracers, discussed in 2) and 3) above. In one embodiment, a combined SPECT-MR tracer is used for registration of an intermediate SPECT image with either a diagnostic or intermediate MR image as discussed in 3) above. The registration procedure can use method M1 or M2. For example, the combined (secondary) tracer may include nanoparticles which are formed from or coated with an MR contrast agent and are also coated with a SPECT contrast agent visible in a SPECT intermediate emission scan. A different (primary) tracer is used for the SPECT diagnostic scan. The primary tracer may include a physiological tracer specific for the region of interest, while the secondary tracer includes a physiological tracer for a closely related area, such as a surrounding bone or tissue. The radiological markers may have different energies.

In general, the acquisition and registration of the MR images and SPECT images includes the following steps:

1. Acquisition of the diagnostic MR images.
2. Immediately before, after or interleaved with the diagnostic MR images, the intermediate non-diagnostic MR images are acquired (where used). Interleaved acquisition tends to minimize patient/organ motion between the acquisitions. The pulse sequence used for the acquisition of the intermediate images can be selected according to the following criteria: same spatial resolution as the SPECT images, i.e. typically 64×64 to 128×128 in-plane resolution, comparable signal-to-noise properties as encountered in the SPECT images, coverage of a field-of-view similar to that of the intermediate SPECT images, and contrast similar to that of the intermediate SPECT images.
3. Acquisition of the diagnostic SPECT images.
4. Immediately before, after, concurrently, or interleaved with the diagnostic images, the intermediate non-diagnostic SPECT images are acquired (where used).
5. Determination of the geometric transformation T that registers the intermediate MR image with the intermediate SPECT image (where an intermediate image is not generated for one modality the transformation registers an intermediate image of the other modality with a diagnostic image). The transformation is generated by the software which includes the mathematical manipulations of the data whereby a number of points in the intermediate images are registered. For example, the software identifies a plurality of corresponding anatomical locations in both images and determines the shift, rotation, scaling, and optionally warping or other non-linear operations to bring the corresponding points into registration. Other image and picture matching techniques are also contemplated. While reference is made to a purely software based registration, all or part of the alignment may include registration by eye, in which a technician superimposes the two images to be registered by moving one or both images until the registrable features overlap. The software may then be used to determine the transformation that the technician has applied.
6. Subjecting the diagnostic MR images to the geometric transformation T. (Alternatively, the transformation could be applied to the SPECT diagnostic image or a transformation applied to both images).
7. After the transformation, combining the MR diagnostic image with the diagnostic SPECT image to form a fused image.

As will be appreciated, the sequence of the above steps can be varied, for example, by performing the SPECT scans prior to the MR scans. Which scan is performed first may depend on the tracers used and their wash out rates. The method can be used in conjunction with any conventional MR and SPECT imaging equipment. The method may be supplemented by further steps, such as enhancement of the SPECT images. For example, a gamma correction, histogram equalization, or other process which enhances the separation of features in the image is performed. The SPECT transmission image, where obtained, may serve both as an intermediate image and also be used for attenuation correction of the diagnostic SPECT image.

The control and processing system 14 can be embodied in a conventional workstation used for the acquisition and analysis of MR and SPECT data. According to the medico-clinical context as determined for example by the diagnostic MR and SPECT data, the pulse sequences appropriate for the acquisition of the intermediate MR images can be automatically selected and fine-tuned using pulse sequence tools already available on MR scanners. The method can be generalized to the registration/fusion of other dual modality images. For example, MR images can be combined with Positron Emission Tomography (PET) images. For such a combination, the above described procedures may be used.

Although the registration can be achieved without recourse to fiducial markers, fiducial markers, detectable in the imaging processes, may also be used to assist in registration of the images.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A system for generating registered nuclear and MR diagnostic images of a subject, the system comprising:
    a nuclear imaging device which generates emission diagnostic images, the nuclear imaging device including a radiation source for use in generating the transmission intermediate images, the transmission image being inherently registered with the emission diagnostic image;
    an MR imaging device which generates magnetic resonance images including magnetic resonance diagnostic images and MR intermediate images, the MR intermediate images being proton density images different from the magnetic resonance diagnostic images, the proton density image being generated by a scan sequence that is interleaved into a scan sequence for generating the MR diagnostic image;
    one or more processors programmed to:
        generate a transform which aligns common anatomical structures in at least one of the nuclear intermediate images generated by the nuclear imaging device and the magnetic resonance images generated by the MR imaging device, and
        applies the transform to bring the emission and magnetic resonance diagnostic images into registration; and
    wherein the transform is generated based on the nuclear intermediate images and the MR intermediate images.

2. A method, for generating registered nuclear and MR diagnostic images of a subject, the method comprising:
    generating an emission diagnostic image and a nuclear intermediate image of the subject with a nuclear imaging device, the intermediate image being an emission image with a differing energy;
    generating at least a magnetic resonance diagnostic image with an MR imaging device;
    generating a transform for aligning common anatomical structures in images generated by the nuclear imaging device and the MR imaging device based on at least the nuclear intermediate image; and applying the transform to bring the emission and magnetic resonance diagnostic images into registration,
wherein the nuclear intermediate image is inherently aligned with the emission diagnostic image and is an emission image and wherein the method further includes:
introducing a radioisotope tracer to the subject, the radioisotope tracer including a radioisotope of a first energy that is preferentially attracted to the anatomical structures that are also imaged by the MR imaging device, and a radioisotope of a second energy that is used for the emission diagnostic image, the generation of the transform including generating the transform from a first energy emission image and an image from the MR imaging device.

3. A method for registration of images of different modalities comprising:
generating a first diagnostic image of a subject with a nuclear imaging process of a first modality;
generating a first intermediate image of the subject with the first modality which is co-registered with the first diagnostic image;
generating a second diagnostic image of a subject with an imaging process of a magnetic resonance modality;
generating a second intermediate image of the subject with the magnetic resonance modality which is co-registered with the second diagnostic image;
deriving a transformation which registers the first and second intermediate images; and
applying the derived transformation to register the first and second diagnostic images.

4. The method according to claim 3, wherein the first diagnostic image is an emission image of a second energy.

5. The method according to claim 3, wherein the first intermediate image is an emission image and the method further includes introducing a radioisotope tracer to the subject, the radioisotope tracer including a radioisotope of a first energy that is preferentially attracted to the anatomical structures that are also imaged by the MR imaging device, and a radioisotope of a second energy that is used for an emission diagnostic image, the generation of the transform including generating the transform from a first energy emission image and an image from the MR imaging device.

6. The method according to claim 3, wherein the second diagnostic image is a magnetic resonance image and the second intermediate image is a magnetic resonance image of lower resolution that the second diagnostic image.

7. The method according to claim 3, further comprising:
introducing a radioisotope to the subject, the radioisotope being associated with a contrast agent which shows in the second intermediate image, the radioisotope showing in the first intermediate image.

8. The method according to claim 3, wherein the second intermediate image is a magnetic resonance image generated by a scan sequence that is interleaved into a scan sequence for generating the second diagnostic image.

9. A system for generating registered nuclear and MR diagnostic images of a subject, the system comprising:
a nuclear imaging device for generating at least emission diagnostic images;
an MR imaging device for generating at least magnetic resonance diagnostic images;
one or more processors programmed to:
generate a transform which aligns common anatomical structures in images generated by the nuclear imaging device and the MR imaging device;
apply the transform to bring the emission and magnetic resonance diagnostic images into registration; and
wherein the MR imaging includes a proton density image different from the magnetic resonance diagnostic image, the proton density image is used to generate the transform for aligning common anatomical structures in images generated by the nuclear imaging device and the MR imaging device.

10. The system according to claim 9, further including:
a radioisotope tracer with the differing energy which is injected into the subject, the radioisotope being preferentially attracted to anatomical structures that are also imaged by the MR imaging device.

11. The system according to claim 9, further including:
a radioisotope tracer which includes a radioisotope of a first energy that is used to generate a nuclear intermediate images and is preferentially attracted to the anatomic structures that are also imaged by the MR imaging device, and a radioisotope of a second energy that is used to generate the emission diagnostic image, the transform being generated from a first energy emission image and an image from the MR imaging device.

12. The system according to claim 11, wherein the magnetic resonance images generated by the MR imaging device include an MR intermediate image and the transform is generated from the first energy emission image and the MR proton density image.

13. The system according to claim 9, further including a radiopharmaceutical which is injected into the subject, the radiopharmaceutical including a radioisotope that is imaged by the nuclear imaging device and a contrast agent that is imaged by the magnetic resonance imaging device.

14. The system according to claim 13, wherein the contrast agent comprises nanoparticles.

15. The system of claim 9, wherein the proton density image is generated by a scan sequence that is interleaved into a scan sequence for generating the magnetic diagnostic image.

16. The system of claim 9, wherein the nuclear imaging device is one of SPECT or PET.

17. The system of claim 9, wherein the nuclear imaging device generates a nuclear intermediate image which is aligned with the MR proton density image.

18. An imaging system comprising:
a nuclear imaging device which generates an emission diagnostic image and a nuclear intermediate image, the intermediate image being one of a transmission image or a differing emission image;
an MR imaging device which generates at least magnetic resonance diagnostic images;
an imaging agent which includes at least a radioisotope tracer with which is injected into the subject, the radioisotope being preferentially attracted to anatomical structures that are also imaged by the MR imaging device; and
one or more processors programmed to:
generate a transform which aligns common anatomical structures in images generated by the nuclear imaging device and the MR imaging device based on at least the nuclear intermediate image; and
applies the transform to bring the emission and magnetic resonance diagnostic images into registration.

19. The imaging system of claim 18, wherein the nuclear imaging device is SPECT.

20. The imaging system of claim 18, wherein the nuclear imaging device is PET.

21. The imaging agent of claim 18, wherein the radioisotope includes a radioisotope of a first energy that is preferentially attracted to the anatomical structures that are also imaged by the MR imaging device, and a radioisotope of a second energy that is used for the emission diagnostic image, the generation of the transform including generating the transform from a first energy emission image and an image from the MR imaging device.

22. The imaging agent of claim 21, wherein the imaging agent includes a contrast agent that is imaged by the magnetic resonance imaging device.

* * * * *